US00PP26111P3

(12) United States Plant Patent
Korlipara

(10) Patent No.: US PP26,111 P3
(45) Date of Patent: Nov. 17, 2015

(54) *ECHINACEA* PLANT NAMED 'DIXIE BELLE'

(50) Latin Name: ***Echinacea* spp.**
Varietal Denomination: Dixie Belle

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 184 days.

(21) Appl. No.: 13/998,593

(22) Filed: Nov. 14, 2013

(65) Prior Publication Data

US 2015/0135384 P1 May 14, 2015

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

Terra Nova Nurseries—Mobile—Introduction—E, retrieved on Jul. 7, 2015, retrieved from the Internet at <http://www.terranovanurseries.com/mobile/pages/introductions_e.html> 3 pp.*

* cited by examiner

*Primary Examiner* — June Hwu
(74) *Attorney, Agent, or Firm* — Klarquist Sparkman, LLP

(57) ABSTRACT

A new and distinct *Echinacea* plant named 'Dixie Belle' characterized by an amazing number of inflorescences starting in the first season, very long bloom time with excellent rebloom, a very upright, compact habit, warm deep pink ray florets surrounding dark cones, numerous, strong dark stems, and excellent vigor.

1 Drawing Sheet

Botanical denomination: *Echinacea* spp.
Variety designation: 'Dixie Belle'.

BACKGROUND OF THE INVENTION

The present invention relates to a new and distinct cultivar of *Echinacea* and given the cultivar name 'Dixie Belle'. *Echinacea* is in the family Asteraceae. The new cultivar is part of a planned breeding program for a landscape series with compact habits and profuse inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Glowing Dream' (U.S. Plant patent application Ser. No. 13/573,330), the new cultivar has wider leaves and inflorescences, and ray florets that are more hot pink in color.

This new *Echinacea* cultivar is uniquely distinguished by:

1. an amazing number of inflorescences starting in the first season,
2. very long bloom time with excellent rebloom,
3. very upright, compact habit,
4. bright warm deep pink ray florets surrounding dark cones,
5. numerous, strong stems, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a group of *Echinacea* 'Dixie Belle' as a two-year-old growing in the trial field in full sun in mid-July in Canby, Oreg.

FIG. 2 shows a single plant dug from this group in the garden.

DETAILED PLANT DESCRIPTION

The following is a detailed description of the new *Echinacea* cultivar based on observations of 18-month-old specimens growing in the garden in July in part sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* $5^{th}$ edition.

Plant:

*Type.*—Herbaceous perennial.

*Hardiness.*—USDA Zones 4 to 9.

*Size.*—Grows to about 37 cm wide and 53 cm tall to top of inflorescences.

*Form.*—Basal clump, with about 7 to 10 stems from the base.

*Vigor.*—Excellent.

*Roots*.—Fibrous, with many downward growing and few laterals, ivory in color, Yellow White 158D, roots develop easily from cuttings from the crown.

Leaf (stem):

*Type*.—Simple.

*Shape*.—Lanceolate.

*Arrangement*.—Alternate.

*Blade size*.—Grows to 11 cm long and 3.5 cm wide.

*Margins*.—Entire to sparsely serrate.

*Apex*.—Acuminate.

*Base*.—Attenuate.

*Surface texture*.—Strigose on both sides.

*Venation*.—Pinnate, Yellow Green 147C on both sides.

*Color*.—Topside Green N137A, bottom side closest to Yellow Green 147A.

*Petiole description*.—Clasping, grows to 3.3 cm long and 3 mm wide, scabrous, narrow leafy edges which fold upwards, topside Green N137A, bottom side closest to Yellow Green 147C.

Inflorescence:

*Type*.—Composite on terminal stalked heads.

*Number of flowering stems from the ground*.—About 10.

*Flowering stem*.—Grows to 50 cm tall from the base of the plant to the terminal inflorescence and can grow to 21.5 cm long from the top stem leaf to the base of an inflorescence; unbranched to branched, with 1 to 9 inflorescences per stem; diameter growing to 7 mm wide near the inflorescence; strigose; Yellow Green 147B.

*Size*.—Grows to 12.5 cm wide and 4 cm deep as disc enlarges.

*Form*.—Ray florets held horizontally, mature disc is conic.

*Immature inflorescence*(*bud*).—2.5 cm wide and 3 cm deep, ray florets held upright at an 75 degrees and rolled up so only the back color shows, Red Purple 70B except tip and main vein Yellow Green 145B, disc color Yellow Green 146B.

*Ray florets*.—Without pistil or stamen, about 20 in number, grow to 55 mm long and 14 mm wide, oblanceolate with the tip two-to-three-toothed (each acute), entire margins, base attenuate, glabrous on both sides; topside new closest to Red Purple 61B; bottom side Greyed Purple 186A, old flowers topside Red Purple 61A, bottom side closest to Red Purple 70A with tip and 3 prominent veins, also 70A.

*Disc*.—Flat becoming conic, becoming 32 mm deep and 35 mm wide with maturity, Greyed Purple 187A in background with bracts Orange 26C with tips Greyed Purple 187A.

*Disc florets*.—About 300 in number, each with 1 pistil and 4 stamen, grow to 10 mm long and 2.5 mm wide, each with one persistent, very stiff linear bract (13 mm long with the top 3 mm Greyed Purple 187A to 5 mm Yellow Green 144A blending to White NN155A on bottom); corolla 6 mm long and 2 mm wide, tubular, 5 lobed, glabrous, Yellow Green 145C tinted Greyed Purple 183B; pistil 10 mm long, ovary 3.5 mm long, White NN155D with top Yellow Green 145B, style 4.5 mm long White NN155A on bottom half and Greyed Orange 177C on top half, 2-branched stigma spreading 2.5 mm wide, Greyed Purple 187A; stamen 5 mm long, filaments 2 mm long and White NN155B, anthers 3 mm long and Greyed Brown N199A, pollen Yellow Orange 20A.

*Involucral bracts*.—In 4 leafy series, area grows to 30 mm wide and 8 mm deep, lobes lanceolate in shape, reflexed, grow to 12 mm long and 4 mm wide, Green N137A, margins strigose, tip acute, strigose on both sides.

*Receptacle*.—Grows to 10 mm wide and 23 mm deep, White NN155B.

*Bloom period*.—July through October in Canby, Oreg.

*Fragrance*.—Floral, sweet, light.

*Lastingness*.—Each inflorescence lasts about two weeks in Canby, Oreg.

Seeds: 3 mm long and 2.5 mm wide, oval, Brown 200C.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

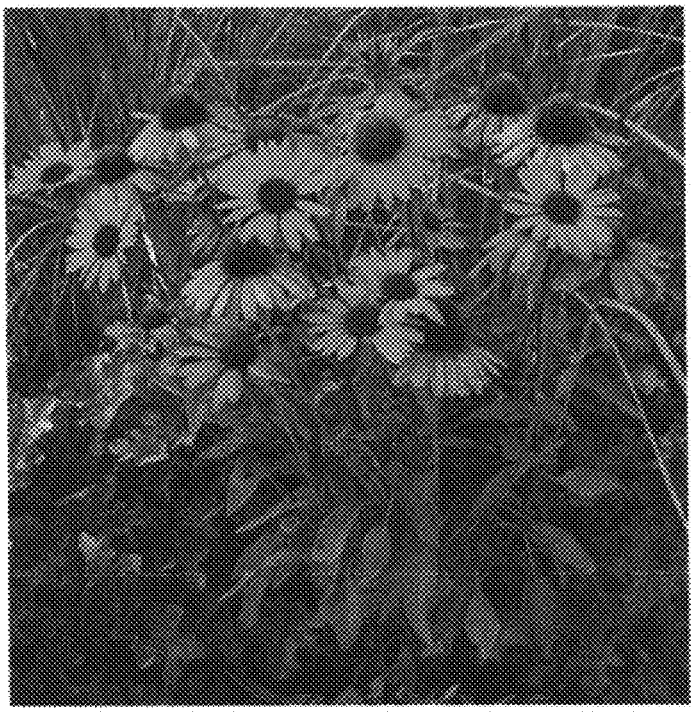

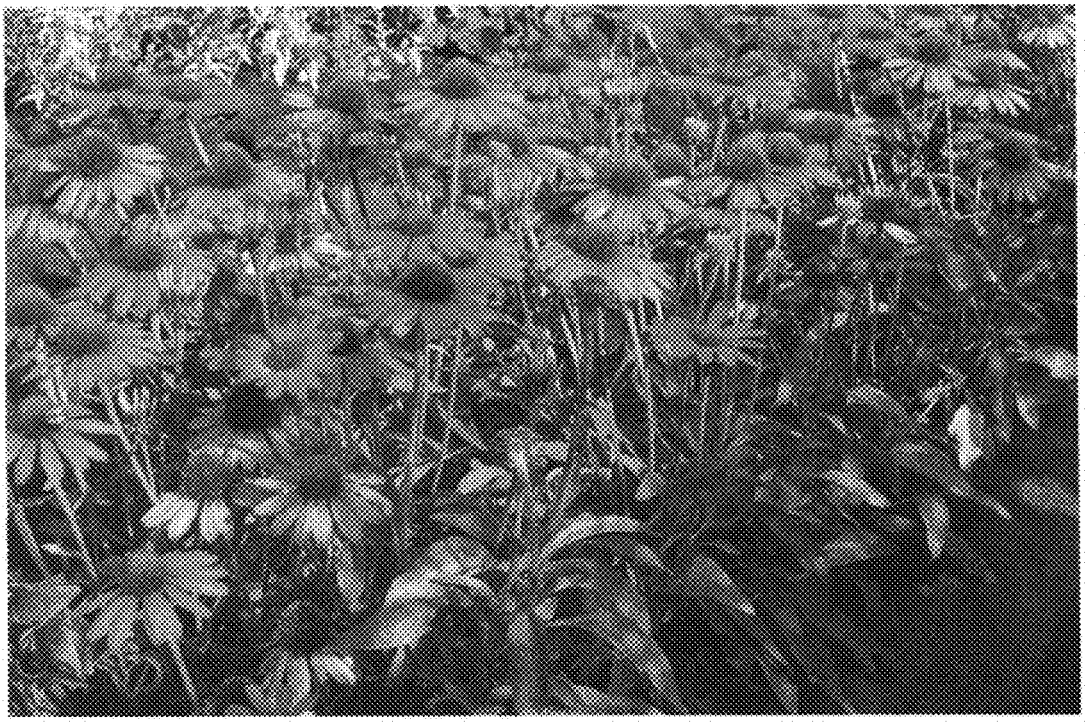
FIG. 1 above, FIG. 2 below